United States Patent [19]

Lavender

[11] 3,973,000
[45] Aug. 3, 1976

[54] PROCESS FOR PURIFIED RABIES VACCINE

[75] Inventor: John F. Lavender, Indianapolis, Ind.

[73] Assignee: Eli Lilly and Company, Indianapolis, Ind.

[22] Filed: July 18, 1975

[21] Appl. No.: 597,054

Related U.S. Application Data

[63] Continuation-in-part of Ser. No. 223,755, Feb. 4, 1972, abandoned.

[52] U.S. Cl. .................................. 424/89; 195/1.5
[51] Int. Cl.$^2$ ...................................... A61K 39/28
[58] Field of Search ...................... 424/89; 195/1.5

[56] References Cited
UNITED STATES PATENTS

| | | | |
|---|---|---|---|
| 2,773,800 | 12/1956 | Powell | 195/1.5 |
| 3,769,415 | 10/1973 | Fenje | 424/89 |

*Primary Examiner*—Shep K. Rose
*Attorney, Agent, or Firm*—Joseph A. Jones; Everet F. Smith

[57] ABSTRACT

An improved purified rabies vaccine is produced by high-centrifugal force centrifugation of the crude egg-embryo-derived vaccine, redispersion of the separated solids, centrifugation of that dispersion at low centrifugal force, and collecting the supernatant.

3 Claims, No Drawings

3,973,000

PROCESS FOR PURIFIED RABIES VACCINE

CROSS-REFERENCE

This application is a continuation-in-part of my copending application Ser. No. 223,755, filed Feb. 4, 1972, now abandoned.

BACKGROUND OF THE INVENTION

The original rabies vaccine of Pasteur, announced in 1885, introduced a new era in medicine. For the first time, it was possible to protect victims of rabid animals from rabies. It was soon realized that the original vaccine, produced in brain tissue, had major disadvantages. The vaccine was very crude, containing high concentrations of neural tissue, lipids, and proteins. Therefore, local and systemic reactions and neuroparalytic accidents were common.

Improved rabies vaccines followed, such as the partially inactivated sheep brain vaccine (1908) and the phenol-inactivated rabbit brain vaccine (1911). Both of these vaccines still caused a significant number of neuroparalytic involvements.

In about 1955, the duck embryo vaccine largely replaced the neural tissue vaccines for human vaccination against rabies in the United States. Neuroparalytic involvements have been virtually eliminated by the embryo vaccine, but local and systemic reactions still occur because of the proteins and lipids in the vaccine.

Rabies vaccine is now ordinarily produced in duck embryos by the elementary process of growing the vaccine in the embryo, harvesting the embryos when optimum virus titer has been achieved, homogenizing the embryos, passing the homogenate through a fine strainer, adjusting the volume to 1 ml. per 200 mg. of embryo tissue and inactivating the virus. The vaccine contains about 10 percent of solids, practically all of it duck tissue, not virus. Therefore, massive amounts of avian proteins and lipids are in the vaccine as it is administered to the patient.

Anaphylactic shock reactions may occur in the patient in at least two ways. At times the vaccine will cause reactions to occur at the first injection. The reactions will be particularly severe in individuals who are for some reason sensitized to avian tissue. Unfortunately, it is necessary to administer repeated doses of the vaccine for protection. Subjects who are to be immunized before exposure must be initially vaccinated with a number of injections of vaccine, and with regular booster doses. Unvaccinated patients who have been bitten by a possibly rabid animal must be vaccinated many times within a short period of time, frequently 14–21 daily doses.

Thus, the duck embryo vaccine, which contains much avian tissue, sensitizes the individual. With each successive dose of the vaccine, or other vaccines of avian origin, it is to be expected that the local or systemic reactions could be more severe and more painful.

The common local reaction occurs as a painful inflammation at the site of injection. More serious reactions involve the organ where the antigen and antibody involved accumulate and react. In the human being, the typical severe reaction is failure of the respiratory function and asphyxiation.

Attempts have been made to produce a rabies vaccine by tissue culture methods, which would provide a vaccine almost free of objectionable host tissues. Such methods so far have usually produced only marginally adequate virus titers.

Another approach to a tissue-free vaccine is to purify the vaccine after it is produced in the normal manner. For example, tissue culture vaccines have been purified by means of centrifugation in a gradient-density medium. Anderson, *Anal. Biochem.* 32, 460 (1968); Lavender et al., *Applied Microbiol.* 22, 358–65 (1971). The gradient-density process effectively removes the antigenic portion of the vaccine from the lighter and heavier portions. However, it requires very precise operation and highly sophisticated controls on the centrifuge and accessories.

SUMMARY

A purified rabies vaccine is produced by centrifugation in two steps. The crude vaccine is centrifuged for the first time at from about 30,000 to about 80,000 G. for from about 15 to about 45 minutes. The solids from that centrifugation are redispersed in a physiologically-acceptable vaccine diluent and the dispersion is centrifuged a second time at from about 500 to about 2,500 G. for from about 2 to about 10 minutes, collecting the supernatant.

DESCRIPTION OF THE PREFERRED EMBODIMENT

I have invented a new and superior method of purifying egg-embryo-derived crude rabies vaccine which consists of:

A. separating the crude vaccine into liquid and solid phases by centrifuging the crude vaccine at from about 30,000 to about 80,000 G. for from about 15 to about 45 minutes;

B. collecting and dispersing the solid phase in a physiologically-acceptable vaccine diluent to product a suspension;

C. separating the suspension into liquid and solid phases by centrifuging the suspension at from about 500 to about 2,500 G. for from about 2 to about 10 minutes; and D. collecting the liquid phase.

A further embodiment of the invention is a purified egg-embryo-derived rabies vaccine, prepared by the following process:

A. infecting embryonated duck eggs with rabies virus;

B. incubating the eggs at about 36°C. for about 14 days;

C. harvesting the embryos from the infected eggs;

D. grinding and dispersing the embryos in a quantity of a physiologically-acceptable vaccine diluent which provides a final dispersed volume of the egg-embryo-derived crude rabies vaccine which does not exceed 1 ml. per 200 mg. of embryos dispersed therein;

E. removing gross amounts of tissue by straining or centrifuging;

F. purifying the crude rabies vaccine by the method described above; and

G. inactivating the vaccine, which inactivation may take place either before or after purifying the vaccine;

each milliliter of which purified rabies vaccine represents at least 200 mg. of embryos, and which vaccine contains less than about 15 mg. of lipids per g. of embryos represented by the vaccine and also contains less than about 2 mg. of protein nitrogen per g. of embryos represented by the vaccine.

Centrifugation is widely used to separate phases having different densities from liquid mixtures. By the proper use of centrifuges, liquids and solids of different densities can be separated from liquids in which the solids are dispersed. The basic principle of centrifugation is the fact that a revolving mass is acted upon by centrifugal force which is proportional to the mass of the object. Therefore, heavier objects, or the more dense of the phases present, are acted upon by greater centrifugal force when a liquid mixture is revolved. Therefore, the more dense phases go to the outside of the revolving mass of the liquid mixture.

Either batch or continuous centrifuges can be used. A typical batch machine is a common laboratory centrifuge which spins the liquid in bottles or tubes. When the bottles are revolved, the more dense phase goes to the outside of the circle of revolution or the bottom of the bottles. The less dense phases go to the top of the liquid mixture. Continuous centrifuges operate on the same principle, but have a rotor so designed that the liquid mixture flows continuously through the rotating parts of the machine. The rotor may consist of a cylinder at the inside of which a layer of the liquid mixture flows, or it may consist of a pair of concentric cylinders, with liquid mixture flowing between them. In any event, means must be provided to keep the phases separate after centrifugal force has separated them. Liquid phases may be removed by takeoff pipes located to pick up the desired phases. A separated solid phase may be removed continuously by appropriate plows or scrapers.

Such continuous removal of solids is not possible in machines operating at very high centrifugal forces, which must be operated as continuous-batch machines. The liquid mixture is pumped into the rotor and separated by centrifugal force. The separated liquids flow continuously out of the machine through one or more takeoff pipes. The solid phase accumulates as an impacted mass against the outer wall of the rotor. Continuous operation is stopped, and the impacted solid phase removed, at appropriate intervals.

Centrifugal force is proportional to the mass of the substance being revolved, proportional to the radius of revolution, and proportional to the square of the speed. The force can be expressed as a pull measured in weight units such as kilograms, but it is more usual to express it as a multiple of the force of gravity (G).

Since centrifugal force is proportional to the radius of the rotating body, one must define the point within the liquid mixture in a centrifuge at which centrifugal force will be measured. For purposes of this specification and claims, centrifugal force will be measured halfway between the inner and outer margins of the liquid mixture. In a continuous or continuous-batch machine, the point of measurement will be the radial center of the layer of liquid mixture. in a batch machine, the point of measurement will be the midpoint of the depth of the liquid mixture in the centrifuge bottles.

The time during which centrifugal force is applied is important. The separation obtained by a given centrifugation is dependent upon the force applied and the time during which it is applied. If the centrifugation is a simple batch process, the time is the time during which the machine is operating. In the case of continuous and continuous-batch machines, an average time concept known as space-time must be used. The space-time during which a continuous process is in operation is found by dividing the volume of the process vessel by the flow rate. For example, if a centrifuge rotor has a capacity of 2,000 ml., and the flow rate is 500 ml./minute, the space-time is 4 minutes. The time of centrifugation will be used here to include the space-time of continuous or continuous-batch processes.

It will be understood by those skilled in the art that all operations described here, in common with all vaccine-production operations, must be conducted under sterile conditions.

The purification method which I have intended is composed of three stages. First, the vaccine is centrifuged at very high centrifugal force. Second, the impacted solid phase from the first centrifugation, which contains proteins and the virus particles which are the active ingredients of the vaccine, is redispersed. Third, the dispersion is centrifuged at low centrifugal force to impact and separate out the proteins. The liquid phase, in which the virus particles are dispersed, is the purified vaccine.

My invention consists in the discovery that the viral portions of a crude rabies vaccine can be separated from the non-antigenic portions of the crude vaccine by specific conditions of centrifugation. I have not invented any centrifugation machinery, nor have I invented the dispersion means or the diluents into which the vaccine is dispersed.

The purification method of my invention begins when a crude egg-embryo-derived rabies vaccine has been prepared and has been strained. The crude vaccine is made by grinding a known weight of infected duck embryos in a suitable diluent, and removing gross amounts of tissue by straining or centrifuging. The standard vaccine is made by grinding 200 mg. into each ml. of vaccine; each ml. of vaccine represents 200 mg. of embryo.

The crude egg-embryo-derived rabies vaccine, after it has been strained, consists of a homogenized mixture of blood and other aqueous-suspended and water-soluble materials, choroid coat materials, lipids, proteins, and a very small proportion of virus particles. The vaccine may be inactivated, if desired, before it starts into my purification process or it may be inactivated after purification.

The first stage of my purification method comprises a centrifugation at centrifugal force from about 30,000 to about 80,000 G. for from about 15 to about 45 minutes. Preferred conditions are from about 45,000 to about 65,000 G. for from about 20 to about 40 minutes. The first centrifugation divides the crude vaccine into one solid and two liquid phases. The lipid phase and the aqueous phase containing hemoglobin and choroid coat float to the inside of the liquid mass. These liquid phases may be exhausted from a continuous or continuous-batch centrifuge and disposed of. In a batch centrifuge, the liquid phases float at the tops of the centrifuge bottles. Care must be taken in a batch centrifuge to stop the machine very smoothly in order to avoid jostling which could cause the liquid phase to be remixed with the solid phase. The solid phase is impacted on the outside of the rotor, or the bottoms of the centrifuge bottles, and is collected for further purification.

After the first centrifugation, the impacted solid phase is dispersed in a physiologically-acceptable vaccine diluent. The dispersion step is necessary to return the impacted mass to a fluid form in which it can be subjected to the second centrifugation.

The dispersion step can be carried out by conventional equipment. In Example 1 below, a Waring blender is used. That device is typical of the devices which are useful for the dispersion. Other types of equipment, such as colloid mills, a simple mortar and pestle, homogenizers (after a preliminary rough-dispersion step), and kinetic dispersion mills are useful devices for the dispersion. The limits on the dispersion process are only those inherent in the production of vaccines: the necessity to maintain absolute sterility of the process; to avoid heating the vaccine; to avoid agitation so violent as to break up the virus particles; and to disperse the proteins and viral particles in the solid phase. Within these limits, any type of dispersion step will serve.

In Example 1 below, the vaccine is dispersed in a diluent which is a 5 percent lactose solution. A number of other useful vaccine diluents are in wide use, and any of them which are normally compatible with a rabies vaccine are entirely satisfactory for use in my method. All of the widely-used vaccine diluents are aqueous solutions of easily water-soluble substances.

Water alone is not often used because the vaccine must be lyophilized to produce a stable product. The lyophilized product is reconstituted before administration to the patient. The original diluent must contain bulking agents such as sugars to assist the vaccine to redisperse when it is reconstituted, and must be tolerated by the patient.

The lactose used in the example below is an excellent addition to a diluent. Other useful diluent bulking agents include sucrose, gelatin, mixtures of gelatin and lactose, and enzymatic digests of casein, such as the widely-used NZ-amine-AS made by Sheffield Chemical Company.

It is possible to adjust the volume in which the protein and viral mass is dispersed. The standard vaccine represents 200 mg. of avian embryo tissue per 1 ml. of vaccine. It is convenient to make purified vaccines either more or less concentrated than standard by changing the final volume of the purified vaccine. For example, the purified vaccine can be made twice as concentrated as standard by dispersing it in a volume which represents 400 mg. of tissue per 1 ml. Such a vaccine can be referred to as a 2X vaccine. Examples 8, 9, and 10 below show the exceptional freedom from anaphylactic shock, combined with good immunizing effect, of a 2X vaccine purified by my method.

The dispersion composed of the solid phase from the first centrifugation dispersed in an appropriate diluent is subjected to a second stage of centrifugation. The second centrifugation is performed at low centrifugal force from about 500 to about 2,500 G. for from about 2 to about 10 minutes. Preferred conditions are from about 1,000 to about 2,000 G. for from about 4 to about 8 minutes. The second centrifugation separates the proteins left from the original crude vaccine from the viral portions of the purified vaccine. The heavy protein substances are impacted, while the viral particles remain suspended in the diluent. The purified vaccine is recovered either by collecting the liquid phase as it flows from a continuous or continuous-batch centrifuge, or by decanting the supernatant if the second centrifugation is done in a batch centrifuge.

It is possible though not advantageous to vary the order of the centrifugation steps. For example, the low-centrifugal-force step which separates the proteins from the virus particles could be done first. The liquid phase from that step, containing the virus particles and the waste liquid phases, could then be centrifuged at high force to impact the virus particles. It would be found, however, when the impacted mass had been dispersed, that a second low-force centrifugation would be necessary to clarify the dispersion by impacting residual tissue debris.

It will be clear to those skilled in processing by centrifugation that the time of centrifugation and force interrelate. It is known that comparable results will often be obtained by a longer time of processing at a lower force and by a shorter time of processing at a higher force. That is, the separation effected by centrifugation is brought about by a force acting over a period of time. A lesser force acting for a longer period of time will, within limits, produce the same result as a greater force over a shorter period of time.

The centrifugations of my method illustrate the point. The first stage of my process demands centrifugation at a force no less than about 30,000 G. If such a force is chosen, then a processing time, or space-time, near the upper end of the range of from about 15 to about 45 minutes should be used. If, on the other hand, a force at or near the maximum force of about 80,000 G. is used, then a processing time near the minimum of the time range should be used.

The extent to which my method purifies egg-embryo-derived rabies vaccines may be measured by determinations of lipid and protein nitrogen content. The following table compares these contents of standard and purified 2X vaccines.

|  | Standard | 2X Purified |
|---|---|---|
| Lipid, mg./ml. | 10 | 3 |
| Protein nitrogen, mg./ml. | 1.5–2.0 | 0.25–0.40 |
| Embryo tissue represented, mg./ml. | 200 | 400 |
| Lipid/embryo tissue, mg./g. | 50 | 7.5 |
| Protein nitrogen/ embryo tissue, mg./g. | 7.5–10 | 0.625–1.0 |

As Examples 8, 9, and 10 prove, the greatly reduced amount of tissue in vaccine purified by my method is very advantageous. Adverse reactions and sensitization reactions to the purified vaccine are much less frequent than are reactions to crude vaccines.

A complete process for the manufacture of a purified egg-embryo-derived rabies vaccine will be shown. I do not mean to imply that the entire process of manufacture of rabies vaccine is my invention. My invention is only the method of purification of the vaccine, and is equally operable whatever process may be used up to the point of purification. The entire process is shown only in order to enable the reader to practice my purification process.

EXAMPLE 1

A crude virus vaccine is grown in duck embryos by the following process. A seed virus, identified as the CVS strain and obtainable from the American Type Culture Collection, 1230 Parklawn Blvd., Rockville, Md. 20852, as culture VR 136, is grown in live mice. After the mice have exhibited symptoms of rabies for one day, their brains are harvested and made into a 20 percent suspension with 2 percent calf serum. That seed suspension is diluted, one part to 50 parts, in distilled water containing 2 percent calf serum.

The diluted suspension is inoculated into duck eggs containing 7-day-old embryos. The air-sac end of the eggs is sterilized with iodine and alcohol, and small holes are drilled through the shell. Approximately 0.2 ml. of the diluted virus suspension is deposited through the air-sac into the amniotic cavity of the egg. The eggs are then allowed to incubate for about 14 days at about 36°C.

At the end of 14 days, the embryos are removed aseptically from the eggs and placed in individual jars. They are individually sterility tested, and frozen in dry ice.

When a batch of vaccine is to be made, 6,600 g. of embryos which pass the sterility test are partially thawed and charged into an Eppenbach colloid mill. To the embryos is added 660 ml. of a sterile 10 percent gelatin solution, 525 ml. of a sterile antioxidant solution containing about 10 percent of cysteine hydrochloride and about 10 percent of potassium dihydrogen phosphate at a pH of about 7.6, and about 8500 ml. of sterile 5 percent lactose solution. The mixture of embryos is ground in the mill for a total of 25 minutes, reducing the clearance between the rotor and stator of the mill from an original setting of 5 mm. to a final setting 1 mm. The vaccine is collected at a final temperature of 22°C. and placed in 500 ml. centrifuge bottles.

The bottles are centrifuged for 10 minutes at 900 rpm, and then the bottles are placed in a stockpot of ice for 30 to 60 minutes. The supernatant from the centrifuge bottles is strained through a 170 mesh nylon filter cloth. The suspension is diluted to a final volume of 30 liters with sterile 5 percent lactose solution.

At this point my purification process begins.

A continuous-batch centrifuge is then set up. The centrifuge is equipped with a rotor having a mid-annulus diameter of 11 cm., capable of at least 30,000 rpm. The rotor, pump, and all transfer lines of the centrifuge are sterilized with formalin, neutralized with 4 percent sodium bisulfite and thoroughly rinsed with sterile water. All lines are then emptied.

The crude vaccine is then centrifuged. The centrifuge is accelerated smoothly to 30,000 rpm (55,335 G.). The vaccine flow is begun slowly as the rotor reaches 10,000 rpm, and both vaccine flow and rotor speed are increased until the flow is 7 liters per hour (equal to 31 minutes spacetime) and rotor speed is 30,000 rpm.

When all of the vaccine has been pumped through the rotor, the pump is stopped before any air enters the rotor. The centrifuge is then allowed to stop without use of a brake, and the rotor is drained from the bottom.

The rotor is then removed from the centrifuge and placed in a sterile hood. The rotor is disassembled, and the impacted solids from the outside of the rotor are transferred into Waring blender jars.

About 250 ml. of sterile 5 percent lactose diluent solution is added to each jar, and the mixture is blended for 2 or 3 minutes.

The virus dispersion is transferred to a calibrated carboy, and the blender jars are rinsed into the carboy. The same diluent solution is added to the dispersed virus suspension to make a total volume of 15 liters (half the original volume of the crude vaccine).

The vaccine is centrifuged again. A similar continuous-batch centrifuge, completely sterilized as before, is used. The rotor speed is 5,000 rpm (1,535 G.) and the flow rate is 36 liters/hour (6 minutes space-time). The liquid supernatant from the centrifuge is the purified vaccine.

The purified vaccine is then inactivated by the addition of 1 ml. $\beta$-propiolactone to each 8 liters of vaccine.

The vaccine is stored at approximately 4°C. for potency testing, innocuity testing, sterility testing, packaging, and lyophilization.

The examples which follow are offered to illustrate other effective methods of carrying out my process of purifying rabies vaccine. It is to be understood that, in each example, the vaccine may be redispersed to any desired volume, to produce a vaccine of the desired concentration.

| Centrifuge Type | First Stage Conditions | Second Stage Conditions |
|---|---|---|
| Example 2 | | |
| continuous-batch | 30,000 G. for 45 minutes | 500 G. for 10 minutes |
| Example 3 | | |
| batch | 80,000 G. for 15 minutes | 2,000 G. for 2 minutes |
| Example 4 | | |
| continuous-batch | 50,000 G. for 35 minutes | 2,000 G. for 4 minutes |
| Example 5 | | |
| batch | 40,000 G. for 35 minutes | 1,000 G. for 8 minutes |
| Example 6 | | |
| continuous-batch | 70,000 G. for 20 minutes | 750 G. for 9 minutes |
| Example 7 | | |
| continuous-batch | 50,000 G. for 30 minutes | 1,500 G. for 5 minutes |

Vaccines produced by my method of purification have consistently passed the potency tests and innocuity tests prescribed by the National Institutes of Health for rabies vaccines.

A purified rabies vaccine made by my process has been tested to prove its freedom from anaphylactic shock reactions by the following test.

EXAMPLE 8

Guinea pigs were used in a test for anaphylactogenic activity of a conventional crude duck embryo rabies vaccine and of a purified vaccine produced from the same type of crude vaccine. Groups of guinea pigs were inoculated subcutaneously with a sensitizing dose of 0.1 ml. each of one of the two vaccines. From 26 to 30 days later, each group of guinea pigs, together with an uninoculated control group, was divided into two groups, each of which was challenged intraveneously with 1 ml. of the same vaccine or the other vaccine. All of the guinea pigs were individually observed for 2 to 5 minutes after challenge and scored. A score of 0 indicates no anaphylactic shock symptoms. A maximum anaphylactic shock was scored 4. Scores of 1, 2, and 3 indicate intermediate degrees of anaphylactic shock.

None of the control animals, for which the 1 ml. challenge dose was the first vaccination, exhibited any anaphylactic shock.

Seven guinea pigs, all those tested, which received a sensitizing dose of crude rabies vaccine, and a challenge dose of the same vaccine, died within 3 minutes of anaphylactic shock which was scored at 4.

Eleven guniea pigs which were sensitized with a purified 2X rabies vaccine, and were then challenged with the same vaccine, exhibited no symptoms of anaphylactic shock. No animal which was both sensitized and challenged with the purified vaccine exhibited any anaphylatic symptoms.

Two animals sensitized with crude vaccine and challenged with 2X purified vaccine had severe shock rated 3 and 4.

Two animals which were sensitized with 2X purified vaccine and challenged with crude vaccine exhibited no anaphylactic shock symptoms.

The typical anaphylactic shock reaction observed in these tests consisted of severe respiratory symptoms.

Purified vaccines made by my method have been tested and shown to be effective in inoculation of humans against rabies. In each example below, a 2X vaccine purified by my method was used.

EXAMPLE 9

Twenty people were given a series of 7 daily 1 ml. subcutaneous injections of purified rabies vaccine. All of the patients were examined daily.

No constitutional reactions occurred. Mild to moderate local reactions occurred in approximately one-half of the individuals, beginning at about the time of the fifth injection and ending approximately 2 days after the last injection. In no instance were the reactions incapacitating.

Blood specimens were obtained before the first dose and on the 4th, 7th, 10th, and 14th day of the study. The blood specimens were examined by standard tests for the determination of rabies antibody.

The standard test is performed by serially diluting a serum sample from the patient. Approximately 50 mouse $LD_{50}$ of fixed rabies virus is added to each diluted sample, and the samples are incubated. Then each sample is injected into a group of mice.

If the patient has developed rabies antibodies, his serum will neutralize the added live fixed rabies virus and the mice will not develop rabies. The dilution which protects 50 percent of the injected mice is computed, and the reciprocal of the dilution is reported as the titer.

Results of the serologic study are shown in the table below. The table also shows results from published data on patients who received conventional, unpurified rabies vaccine.

|  | 10 day data | 14 day data |
|---|---|---|
| Purified 2X vaccine (7 doses) | | |
| Conversion | 17/ 19 (89%) | 19/ 19 (100%) |
| Titer < 16 | 12/ 17 (71%) | 6/ 19 (32%) |
| ≥ 16 | 5/ 17 (29%) | 13/ 19 (68%) |
| > 32 | 2/ 17 (12%) | 6/ 19 (32%) |
| Conventional vaccine (14 doses) | | |
| Conversion | 86/104 (83%) | 100/102 (98%) |
| Titer < 16 | 61/ 86 (71%) | 44/100 (44%) |
| ≥ 16 | 25/ 86 (29%) | 56/100 (56%) |
| > 32 | 8/ 86 (9%) | 36/100 (36%) |

The data shows that the purified 2X vaccine produced immunity after 7 doses equal to that produced by 14 doses of conventional vaccine.

EXAMPLE 10

A group of 156 patents were administered a series of five 1 ml. subcutaneous injections. Four injections were given one week apart and the 5th was administered 4 to 6 months later as a booster dose. The series of injections is typical of preexposure immunization vaccination against rabies.

Less than 10 percent of the individuals exhibited any detectable local erythema, induration, or adenopathy. Less than 2 percent of these consisted of erythema and induration greater than 3 cm. There were no constitutional reactions, and there was no indication that reactivity increased with successive doses.

I claim:
1. A method of purifying an egg-embryo-derived crude rabies vaccine which consists of:
   A. separating the crude vaccine into liquid and solid phases by centrifuging the crude vaccine at from about 30,000 to about 80,000 G. for from about 15 to about 45 minutes;
   B. collecting and dispersing the solid phase in a physiologically-acceptable vaccine diluent to produce a suspension;
   C. separating the suspension into liquid and solid phases by centrifuging the suspension at from about 500 to about 2,500 G. for from about 2 to about 10 minutes; and
   D. collecting the liquid phase.
2. A method of claim 1 which consists of:
   A. centrifugation at from about 45,000 to about 65,000 G. for from about 20 to about 40 minutes;
   B. collecting and dispersing the solid phase in a physiologically-acceptable vaccine diluent to produce a suspension;
   C. centrifugation at from about 1,000 to about 2,000 G. for from about 4 to about 8 minutes; and
   D. collecting the liquid phase.
3. A purified egg-embryo-derived rabies vaccine, prepared by the following process:
   A. infecting embryonated duck eggs with rabies virus;
   B. incubating the eggs at about 36°C. for about 14 days;
   C. harvesting the embryos from the infected eggs;
   D. grinding and dispersing the embryos in a quantity of a physiologically-acceptable vaccine diluent which provides a final dispersed volume of the egg-embryo-derived crude rabies vaccine which does not exceed 1 ml. per 200 mg. of embryos dispersed therein;
   E. removing gross amounts of tissue by straining or centrifuging;
   F. purifying the crude rabies vaccine by the method of claim 1; and
   G. inactivating the vaccine, which inactivation may take place either before or after purifying the vaccine;

each milliliter of which purified rabies vaccine represents at least 200 mg. of embryos, and which vaccine contains less than about 15 mg. of lipids per g. of embryos represented by the vaccine and also contains less than about 2 mg. of protein nitrogen per g. of embryos represented by the vaccine.

* * * * *